United States Patent [19]

Tanaka

[11] Patent Number: 4,481,227
[45] Date of Patent: Nov. 6, 1984

[54] METHOD OF COLORING BAKEABLE PORCELAIN DENTAL RESTORATIONS

[76] Inventor: Asami Tanaka, 9307 N. Lavergne, Skokie, Ill. 60077

[21] Appl. No.: 438,252

[22] Filed: Nov. 1, 1982

Related U.S. Application Data

[63] Continuation of Ser. No. 186,757, Sep. 12, 1980, abandoned.

[51] Int. Cl.³ .............................................. A61C 5/10
[52] U.S. Cl. ........................................ 427/2; 433/203
[58] Field of Search ...................... 433/203; 427/376.2, 427/2, 419.3, 419.4

[56] References Cited

U.S. PATENT DOCUMENTS

| | | | |
|---|---|---|---|
| 2,682,480 | 6/1954 | Andrews | 427/376.2 |
| 3,089,782 | 5/1963 | Bush . | |
| 3,218,711 | 11/1965 | Connor | 433/203 |
| 4,107,348 | 8/1978 | Hirschhorn | 427/2 |
| 4,141,144 | 2/1979 | Lustgarter | 433/217 |
| 4,207,678 | 6/1980 | Jeannette | 433/203 |

OTHER PUBLICATIONS

Quintessence of Dental Technology, Hirschhorn, 5/79.
Journal A.D.A., May 1929, Pilkington, pp. 804–812.

Primary Examiner—Sam Silverberg
Attorney, Agent, or Firm—Neuman, Williams, Anderson & Olson

[57] ABSTRACT

A method is provided of coloring bakeable porcelain dental restorations. A plurality of pigmented coloring solutions is provided for application to a porcelain restoration. Each coloring solution comprises a pigment of low temperature porcelain-fusable powder and a substantially clear carrier liquid that supports a dispersion of said pigment and vaporizes when the restoration is baked. A film of the coloring solution is coated onto said restoration and then cured. The steps of coating the restoration and curing the film are repeated as necessary to match the color of the restoration to the color of a patient's teeth. The coated restoration is then baked to fuse the pigment to the porcelain and vaporize the cured carrier liquid.

25 Claims, 2 Drawing Figures

METHOD OF COLORING BAKEABLE PORCELAIN DENTAL RESTORATIONS

This is a continuation of application Ser. No. 186,757 filed Sept. 12, 1980 now abandoned the text of which is hereby incorporated by reference.

BACKGROUND OF THE INVENTION

This invention relates generally to the coloring of dental restorations to match the color of a patient's existing teeth. More particularly it relates to a method of coloring bakeable porcelain dental restorations through the application of a pigment of low temperature procelain-fusable powder dispersed in a substantially clear vaporizable cureable carrier liquid.

It is desireable to match the color of a dental restoration to the color of the patient's existing teeth for aesthetic reasons and to encourage the patient to use the prosthesis. Tooth color varies not only from patient to patient, but also from tooth to tooth on a single patient, and may even vary on a single tooth from side to side or top to bottom. These variations arise from, among other things, smoking, drinking of tea or coffee, variations in dental hygiene or diet, physical injury, or orthodontics. In addition, the teeth of younger patients are generally lighter in color than the teeth of older patients.

In the past, the dentist or technician would attempt to match the color of the existing teeth to one of a finite number of sample colors supplied by a dental laboratory. This limited selection made it possible to approximate the desired color, but very rarely was the dentist able to duplicate the same intensity or hue. Moreover, the color selected was usually uniform over the entire tooth, eliminating the possibility of different shadings or hues for a single tooth. A still further disadvantage was that the laboratory technician would then attempt to duplicate the dentist's chosen color on the actual restoration at a later date, in a laboratory remote from the dentist's office, and without the patient present. All of these disadvantages contributed to undesireable nonuniform and inaccurate color match-ups. Moreover, variations in the type or color of the light used by the dentist and technician, and the position in the mouth of the restored tooth, resulted in still further color variations. Thus, it sometimes became necessary for the patient to visit the dental laboratory on several occasions over a period of several days or weeks for a trial and error method of coloration. This was time consuming, costly, and exasperating for both the patient and dentist.

The coloring of porcelain dental restorations was accomplished in the past by applying an appropriate amount of pigment in a water soluble solution and then baking the restoration to permanently impart the color. If, after baking, the color had to be darkened or altered by the addition of more pigment, then the steps had to be repeated as often as necessary until a satisfactory color was obtained. However, if the color was too dark, or the hue could not be altered by the addition of color, an expensive restoration was ruined. Thus, this task required great skill and experience. These problems were heightened by the use of a water solution because the presence of moisture or saliva on the tooth often destroyed or mottled the coloration, and in some instances the application of subsequent coatings before baking would remove, dissolve or otherwise alter the earlier applied coatings. Moreover, coatings that are water soluble often rub off with excessive handling, and they cannot be used in the mouth, making a correct color match at the dentist's office more difficult.

The coloring of acrylic or plastic restorations required the application, to a finished restoration, of a stain or shading compound dissolved in water or a solution that evaporates at room temperature. Although baking is not necessary, these colors are permanent and must be ground off if the color is too dark or cannot be corrected by the addition of more color or stain. In addition, the aforenoted problems associated with moisture and water soluble coatings also apply to acrylic restorations.

SUMMARY OF THE INVENTION

Accordingly, it is a general object of the present invention to provide an improved method of coloring bakeable porcelain dental restorations which achieves the aforesaid desired results and overcomes the aforesaid problems of the prior art.

More particularly, it is an object of the present invention to provide a method for coloring bakeable porcelain dental restorations that permits the dentist to match the color of the restoration to the color of the patient's existing teeth, including color variations within a single tooth and any nonuniform coloration.

It is a further object of the present invention to provide a method that permits the dentist to color the restoration itself with the patient present, by applying the actual pigment to the tooth, wetting it, and comparing it to the patient's existing teeth to insure that the coloration is accurate.

It is a still further object of the present invention to provide a method that permits the dentist to lighten the shade and alter the color as desired, and easily remove the color or even start anew, without ruining the restoration or requiring grinding.

It is a still further object of the present invention to provide a method that permits the dentist to color the restoration itself to provide an exact color rendition while the patient is present, thereby eliminating intermediate color samples, repetitive trial and error applications of coloring and subsequent baking, and minimizing the possibility of a color mismatch.

Other objects and advantages of the invention will become apparent upon reading the following detailed description and appended claims.

These objects are achieved by use of the method of this invention of coloring bakeable porcelain dental restorations, including providing one or more coloring solutions for application to a porcelain restoration. Each solution includes a different pigment for coloring bakeable porcelain and a substantially clear vaporizable cureable carrier liquid to support the pigment. A coloring solution is coated onto at least a portion of said restoration and cured. The steps of coating and curing are repeated as necessary to match the color of the restoration to the color of a patient's teeth. The restoration with the coating is then baked at a temperature sufficiently high to vaporize the carrier liquid and to fuse the pigment to the restoration.

DESCRIPTION OF THE DRAWINGS

For a more complete understanding of this invention, reference should be made to the drawings described below.

DESCRIPTION OF THE INVENTION

Figure 1:
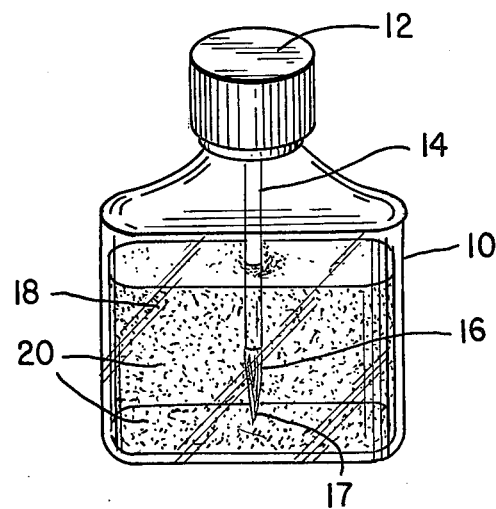
FIG. 1 is a front perspective view of a bottle, including a cap with an attached brush extending down into the bottle, containing a coloring solution. The solution is a substantially clear vaporizable carrier liquid supporting a dispersion of pigment of low temperature porcelain-fusable powder.

Coloration of a bakeable porcelain dental restoration according to the present invention includes providing one or more coloring solutions comprising a pigment coloration and a carrier liquid. Said solutions may be stored in a bottle 10, as shown in FIG. 1, with a cap 12 having an attached brush 14. The brush may comprise any suitable bristles 16, such as camel hair, and is usually tapered to a fine point 17. The container, cap, brush, and bristle shape may be altered as desired and are not part of the present invention.

The pigment coloration may include the three primary colors, red, yellow, and blue, but more commonly include earth tones such as shades of grays, browns, tans, and pinks. In addition, white and blue are useful.

The pigment coloration is a low temperature porcelain-fusable powder commonly used for coloring porcelain by baking. Typically, it is an oxide of such metals as gold, iron, cobalt, or titanium, although many others are equally satisfactory and well known. When heated to temperatures usually greater than 1000° F., the oxide permanently fuses to the ceramic. The pigments may be chosen as desired and mixed to produce any useful colors.

The carrier liquid 18 is a substantially clear vaporizable carrier that supports a dispersion of said pigment 20 and removably binds the pigment to the porcelain once the carrier liquid cures. Referring to FIG. 1, the liquid 18 is shown supporting a dispersion of pigment particles 20. If the pigment should precipitate or settle to the bottom of the bottle 10, it may be redistributed by shaking the bottle and solution. A typical recipe for the coloring solution is 10% to 20% pigment, by weight, with the remainder being carrier liquid. However, this ratio and these proportions may be altered as desired.

The exact composition of the carrier liquid 18 is not critical provided that it is substantially clear, capable of supporting a dispersion of said pigment, cureable, and vaporizable at porcelain baking temperatures (usually over 1000° F.). Substantial clarity is desireable to permit the true pigment color to show and to facilitate an accurate color match between the restoration and the patient's teeth. The solution must be capable of supporting a dispersion of said pigment so that the pigment may be transferred to the porcelain restoration via a brush or other applicator. Curability of the solution is desireable so that additional coatings of coloring solution may be added without disturbing existing coatings. The solution must be vaporizable at the elevated porcelain baking temperatures so that it will burn off, leaving only the pigment, which fuses to the porcelain to permanently impart the selected coloration.

Suitable solutions include any of a variety of common liquid plastics that dry relatively quickly, such as liquid acetate. Another suitable carrier liquid is commercially available clear liquid fingernail polish. The carrier liquid may be chosen as desired provided it meets the criteria set forth herein and it may be diluted or thinned as desireable to provide a suitable working medium.

One reason liquid plastics have been found particularly suitable is because they dry or cure relatively quickly, i.e. usually in less than a minute at room temperature. This permits rapid and accurate coloring of the restoration while the patient is present. Once cured, it may be recoated without disturbing earlier applied coats. The cured plastic coating may also be easily removed by scraping with an instrument or fingernail to remove undesired pigment without damaging the underlying restoration. The cured plastic is also impervious to water and may be wet with saliva to more accurately assess the color match to the patient's teeth.

Figure 2:
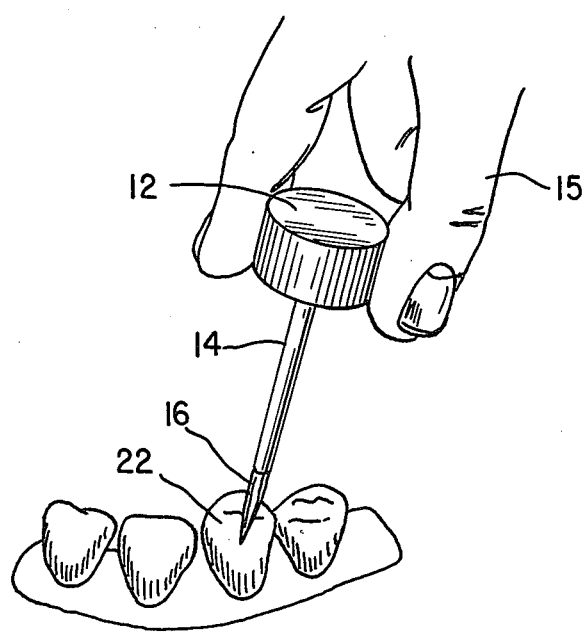
FIG. 2 is a perspective view showing the use of a brush to coat a film of said coloring solution onto a bakeable porcelain dental restoration.

The color of the porcelain restoration is changed by coating a film of one of the coloring solutions onto the porcelain restoration as shown in FIG. 2. Typically, the brush and cap combination, numbers 12 and 14, is grasped by the dentist's hand 15. The pigmented coloring solution clings to the bristles 16 and is coated onto all or a portion of the porcelain restoration 22 with strokes of the brush.

After application, the pigmented coating cures relatively quickly. If the carrier liquid is a liquid plastic or the like, it typically cures in less than a minute, and often in a matter of seconds. If desired, any portion of coating and the pigment bound thereby may be removed by scraping with an instrument. This ease of removal of the coloring solution assists in creating variations in shading and permits one to remove all or any part of the applied pigment to lighten coloration that is too dark. This may be done at any time until the restoration is baked and the pigment is permanently fused. On the other hand, additional coats of the same or different pigmented colors may be applied to alter or darken the color. Subsequent applications will not disturb existing coats. The steps of application, curing, and, if desireable, removal of the coloring solution and pigment, may be repeated as necessary or desireable to obtain the proper coloration.

Once the desired color is obtained, the dentist may wet the film coated porcelain with water or saliva to more accurately check the color match with the patient's teeth. This entire process can be completed in a single visit to the dentist and eliminates subsequent appointments and delays to recheck or darken initial color matching attempts.

The color is permanently fused to the porcelain by baking the restoration with the coating or coatings of cured coloring solution at a temperature sufficiently high to vaporize the carrier liquid, and fuse the pigment to said restoration. This eliminates the carrier solution and permanently colors the restoration. The restoration is now ready for any finishing steps prior to use by the patient.

In the event additional coloration is desired, the coating, curing, and baking steps may be repeated as often as desired.

As set forth, many modifications and alternate embodiments of the subject invention will readily come to one skilled in the art having the benefit of the teachings presented in the foregoing description in accompaniment with the associated drawings. Therefore it is to be understood that the invention is not to be limited thereto and that said modifications and embodiments are inteded to be included within the scope of the appeneded claims.

What is claimed is:

1. A method of coloring the porcelain of bakeable porcelain dental restorations, comprising:
 (a) providing cureable coloring solutions for application to the non-metallic porcelain portion of said restoration, each solution comprising a different color pigment of low temperature porcelain-fuseable powder and a substantially clear vaporizable cureable carrier liquid to support a dispersion of said pigment, said carrier liquid being impervious to water or saliva when cured;

(b) coating at least a portion of said porcelain restoration with a film of one of said coloring solutions to closely match the color of said restoration to the color of a patient's existing tooth;

(c) curing said film at non-elevated temperatures on said porcelain restoration prior to the application of a subsequent film, said cured film being substantially clear, dry, impervious to water or saliva, undisturbed by handling and capable of being recoated without disturbing earlier applied and cured coats;

(d) recoating at least a portion of said previously applied and cured film with a predetermined number of said coloring solutions until a desired coloration is obtained, each film recoating being cured prior to the application of a subsequent film coating whereby each previous film coating is not disturbed by a subsequent film coating; and (e) baking said restoration with said predetermined number of films thereon at a temperature sufficiently high to vaporize said carrier liquid and to fuse said pigment to said restoration, thereby permanently coloring said restoration.

2. The method of claim 1 wherein said pigment comprises a metal oxide suitable for use with porcelain.

3. The method of claim 1 wherein said carrier liquid vaporizes at a temperature approximately equal to or less than the temperature at which said pigment fuses to said restoration.

4. The method of claim 1 wherein said pigment fuses to said porcelain at a temperature greater than about 1000° F.

5. The method of claim 1 wherein said carrier liquid is an organic material.

6. The method of claim 1 wherein said carrier liquid vaporizes at a temperature of about 1000° F.

7. The method of claim 1 wherein said carrier liquid is not soluble in water or saliva.

8. The method of claim 1 wherein said carrier liquid comprises at least in part, liquid acetate.

9. The method of claim 1 wherein said carrier liquid cures at room temperature.

10. The method of claim 1 wherein said carrier liquid cures in less than one minute when coated on a substrate.

11. The method of claim 1 wherein said coloring solutions are coated on said restoration with a brush-like applicator.

12. The method of claim 1 wherein the curing of said coating of said coloring solution removably binds said pigment to said procelain.

13. The method of claim 1 wherein portions of said coating of cured solution are manually removed without damaging the underlying porcelain substrate.

14. A method of coloring bakeable procelain dental restorations, comprising:

(a) providing cureable coloring solutions for application to the porcelain of said restoration, each solution comprising a different color pigment of low temperature porcelain-fusable powder and a substantially clear fast-curing vaporizable carrier liquid to support a dispersion of said pigment, said carrier liquid being impervious to water or saliva when cured;

(b) coating at least a portion of said porcelain restoration with a film of one of said coloring solutions to alter the color of said porcelain restoration to closely match the color of a patient's existing tooth;

(c) curing said applied film at non-elevated temperatures prior to the application of a subsequent film, said cured film being substantially clear, dry, impervious to water or saliva, undisturbed by handling and capable of being recoated without disturbing earlier applied and cured coats;

(d) manually removing any unnecessary portion of said coating of cured solution;

(e) recoating at least a portion of said previously applied and cured film with a predetermined number of films of one or more of said coloring solutions until a desired coloration is obtained, each film coating being cured prior to the application of a subsequent film coating whereby a previously applied film is not disturbed by a subsequent coating; and (f) baking said restoration with said predetermined number of films thereon at a temperature sufficiently high to vaporize said carrier liquid and to fuse said pigment to said restoration, thereby permanently coloring said restoration.

15. The method of claim 14 wherein said pigment comprises a metal oxide suitable for use with porcelain.

16. The method of claim 14 wherein said carrier liquid vaporizes at a temperature approximately equal to or less than the temperature at which said pigment fuses to said restoration.

17. The method of claim 14 wherein said pigment fuses to said porcelain at a temperature greater than about 1000° F.

18. The method of claim 14 wherein said carrier liquid is an organic material.

19. The method of claim 14 wherein said carrier liquid vaporizes at a temperature of about 1000° F.

20. The method of claim 14 wherein said carrier liquid comprises at least in part, liquid acetate.

21. The method of claim 14 wherein said carrier liquid cures at room temperature.

22. The method of claim 14 wherein said carrier liquid cures in less than one minute when coated on a substrate.

23. The method of claim 14 wherein said coloring solutions are coated on said restoration with a brush-like applicator.

24. The method of claim 14 wherein the curing of said coating of said coloring solution removably binds said pigment to said procelain.

25. The method of claim 14 wherein portions of said coating of cured solution are manually removed without damaging the underlying porcelain substrate.

* * * * *